United States Patent [19]
Seden et al.

[11] Patent Number: 5,293,186
[45] Date of Patent: Mar. 8, 1994

[54] CONTACT LENS

[75] Inventors: William E. Seden, Fareham; Ronald S. Hamilton, Southampton Hants, both of England

[73] Assignee: British Technology Group Ltd., London, England

[21] Appl. No.: 867,684

[22] PCT Filed: Nov. 6, 1990

[86] PCT No.: PCT/GB90/01699
§ 371 Date: Jul. 9, 1992
§ 102(e) Date: Jul. 9, 1992

[87] PCT Pub. No.: WO91/07687
PCT Pub. Date: May 30, 1991

[30] Foreign Application Priority Data

Nov. 8, 1989 [GB] United Kingdom ............... 8925246

[51] Int. Cl.$^5$ .............................................. G02C 7/04
[52] U.S. Cl. ........................... 351/160 R; 351/160 H; 351/177
[58] Field of Search ............... 351/160 R, 160 H, 161, 351/162, 177

[56] References Cited

U.S. PATENT DOCUMENTS

| | | | |
|---|---|---|---|
| 3,227,855 | 1/1966 | Meyer, Sr. et al. | 219/384 |
| 3,228,741 | 1/1966 | Becker | 351/160 R |
| 3,833,786 | 9/1974 | Brucker | 219/121 L |
| 3,871,910 | 3/1975 | Barkis et al. | 117/38.8 E |
| 3,971,910 | 7/1976 | Marschalko | 219/121 L |
| 4,068,933 | 1/1978 | Seiderman | 351/160 R |
| 4,466,705 | 8/1984 | Michelson | 351/160 H |
| 4,563,565 | 1/1986 | Kampfer et al. | 219/121 LJ |
| 4,571,039 | 2/1986 | Poler | 351/160 R |
| 4,621,912 | 11/1986 | Meyer | 351/160 R |
| 4,709,996 | 12/1987 | Michelson | 351/160 H |
| 4,994,080 | 2/1991 | Shepard | 351/160 R |
| 5,061,057 | 10/1991 | Kumakura et al. | 351/160 R |
| 5,104,213 | 4/1992 | Wolfson | 351/160 H |

FOREIGN PATENT DOCUMENTS

| | | |
|---|---|---|
| 0042679 | 12/1981 | European Pat. Off. |
| 0367513 | 5/1990 | European Pat. Off. |
| 826204 | 12/1951 | Fed. Rep. of Germany |
| 922871 | 4/1963 | United Kingdom |
| 2152698 | 8/1985 | United Kingdom |

OTHER PUBLICATIONS

Wichterle et al "Perforated Soft Hydrogel..." International Eyecare, vol. 1, No. 4, Sep. 1985, pp. 315–318.

Hill et al "Respiratory Profiles of the Corneal..." American Journal of Optometry & Archives of American Acad. of Optometry, Jun. 1967, pp. 365–373.

R. M. Hill et al. "Respiratory Profiles of the Corneal..." American Jour of Optometry & Arch. of Ame. Acad of Optometry, Jun. 1967, pp. 365–379.

O. Wichterle et al. "Perforated soft hydrogel contact lenses" International Eyecare, vol. 1 No. 4, Sep. 1985, pp. 315–318.

*Primary Examiner*—Scott J. Sugarman
*Attorney, Agent, or Firm*—Nixon & Vanderhye

[57] ABSTRACT

To improve its gas-permeability, a contact lens, which may be of any normal material, even a gas-impermeable material such as polymethylmethacrylate, is microperforated with 66000 holes distributed in equispaced sectors leaving unperforated the central (optically important) part and the outermost rim of the lens. With a smaller hole size, some one million holes can be accommodated. In a modification, some or all of the holes go only part way through the thickness of the contact lens.

42 Claims, No Drawings

CONTACT LENS

FIELD OF THE INVENTION

This invention relates to a contact lens and in particular to ways of increasing the gas permeability of a contact lens.

A hard contact lens such as of polymethyl-methacrylate has advantages of longevity, biocompatability, strength, durability, wettability and the ability to mask up to a certain degree of astigmatism but has the drawback of effectively starving the cornea surface of oxygen. This leads to oedema (thickening of the cornea) and other undesirable effects.

A soft contact lens such as of a hydrogel has advantages of oxygen permeability and comfort but is in turn susceptible to accumulation of proteins and other deposits, and is required to be kept scrupulously clean and sterile.

The present invention proposes to combine these advantages as appropriate, by enhancing the oxygen permeability of any contact lens material.

DESCRIPTION OF THE PRIOR ART

To avoid oedema, it has been proposed in U.S. Pat. No. 3833786 to fenestrate a contact lens by holes sufficiently large for bulk tear flow to take place through them, thus transferring sufficient dissolved oxygen to the eye surface. This is expensive and difficult to achieve consistently and may impair the perceived clarity of the contact lens. Various techniques have been proposed for the fenestration of contact lenses. One system (U.S. Pat. No. 3,227,855) uses a spark to locally burn a small hole through the lens and others (U.S. Pat. No. 3,833,786 above and U.S. Pat. No. 3,971,910) describe laser based systems. The lasers described are of the $CO_2$ type in which a concentrated beam is used to burn through the lens to produce the holes.

These patents start from the basis that the fenestration itself is to provide a path for tears to flow through the lens enabling fresh oxygenated tears to feed the cornea. Most experiments have accordingly been conducted on lenses with a few (generally less than 10) large diameter (generally greater than 200 microns) holes. Wichterle and Krejci (International Eyecare, September 1985 page 315) recommended contact lens perforation in the center only, i.e. the optically most disadvantageous location. Hill & Leighton (Americal Journal of Optometry And Archives of American Academy of Optometry, June 1967 page 365) conclude that no corneal benefit results (even directly under the hole) from a 1.0 mm hole nor from holes as small as 25 microns. These latter holes were spark generated at a density of $3/mm^2$. There has thus been every reason to abandon the concept of fenestrating contact lenses, especially with small holes.

SUMMARY

According to the present invention, a contact lens has holes going part or all the way from one lens surface towards the other, in sufficient number to account for at least 5%, preferably at least 10%, more preferably at least 15%, most preferably at least 20%, optionally at least 25%, generally at least 30%, desirably at least 35% and suitably at least 40% of the area of the lens. The holes may be provided over the whole area of the lens, or in the peripheral part of the lens, or in the central region of the lens, preferably substantially uniformly over the relevant specified area, with preferably substantially no holes elsewhere. The peripheral part of the lens is deemed to be that outside a central region of 5-11 (e.g. 7-9) mm diameter, within which there are preferably fewer (e.g. under 0.7, 0.6 or $\frac{1}{2}mm^2$ altogether) or no holes. There may be at least 2000 of these holes and preferably over 5000 holes more preferably over $10^4$, most preferably over $5 \times 10^4$ possibly over $10^5$ such as over $5 \times 10^5$ holes, even over $10^6$ holes.

The holes may be smaller than diameter 150 μm (e.g. smaller than 100 μm, preferably smaller than 50 μm, more preferably smaller than 30 μm, ideally smaller than 10 μm) e.g. under $50 \times 10^{-5} mm^2$ more preferably under $20 \times 10^{-5} mm^2$ optionally under $10 \times 10^{-5} mm^2$, desirably under $5 \times 10^{-5} mm^2$, if possible under $2 \times 10^{-5} mm^2$ in area, or the holes are in a variety of these sizes. Smaller holes are considered likely to be more comfortable to the lens wearer. The holes go from one lens surface towards the other. The holes may be blind or may interconnect the two lens surfaces or there may be some of each. The blind holes if any may start from the convex or the concave surface or some of each, preferably from the concave surface, whereby the eyelid nerves, which have been found to be more sensitive than the cornea, are not aggravated, there is no risk to the appearance of the lens and deposits will not lodge in the holes. These holes are conveniently machined many, several or all at a time by an excimer laser. If only the peripheral part of the lens is machined, this may be done in sectors. This has the advantage that the hole axes of each sector, i.e. the laser direction, can be more closely approximated to the normal to the surface of the lens in the middle of each sector, lessening any optical interference by the holes and minimising the distance for oxygen transport. Both the wearer and any observer can be unaware of the fact that the lens has these holes. Part drilled holes are ideally produced by excimer laser which is a pulse type laser. Each pulse ablates a fixed amount, or depth, of material. Typically, 120 pulses are required to drill through a 0.1 mm thick contact lens. Lenses have been part drilled using 50, 70, 80, 90, 100 and 120 pulses thus producing holes 42%, 58%, 67%, 75%, 83% and 100% through the thickness of the lens.

It may be advantageous to vary the depth of the part drilled holes across the surface of the lens in proportion to the lens thickness (for example using an iris mechanism coupled to the laser mask). This would tend to a more uniform distribution of oxygen transmissibility and hence improved corneal health. Alternatively, the (blind) holes could be wider in proportion to the lens thickness at that point and all of the same depth. The hole density (holes/$mm^2$) can also be varied according to the lens thickness to help equalise the oxygen supply.

The excimer laser is preferably applied through a mask and the masked laser beam then focussed on the lens. In this way, the mask, which must mechanically withstand a proportion of the laser output, can be made relatively massive and laser-proof compared with the lens. The mask might not be so durable if used in contact mode with the lens and thus necessarily being much smaller.

The lens is preferably mounted (during this operation) on a radiation-absorbing support e.g. a polypropylene ball. If the support were reflective, laser radiation through a completed hole might scatter off the support, doing random damage to the lens. European Patent Publication 367513A describes a method of manufacture in which the contact lens is cast and retained on a polypropylene mould, ideally suited for presentation to an excimer laser drilling system.

A high output laser is preferred, for speed of production and to reduce the incidence of hole taper; the ratio (laser entrance hole size: laser exit hole size), which should ideally be unity (=parallel-sided hole) increases with lens thickness but does so progressively less as laser power is increased. For example using a laser fluence of $4J/cm^2$, a 22-micron diameter entrance hole will taper to become a 10-micron exit hole when drilled through a 450-micron thick lens. Using the 'mask then focus' technique described above permits an increased power of laser to be used with the advantages of yielding more accurately parallel-sided holes and of reducing the laser-machining time to form the holes. The laser wavelength will be chosen according to the lens material. For those materials in commonest use, a wavelength of 160–230 nm, preferably 185–200 nm was found suitable.

Although the contact lens may be of any material of which such lenses are normally made, according to the clinical requirements of the wearer, an advantageous material is hydroxyethylmethacrylate. This combines a certain degree of softness and inherent oxygen permeability with some strength and durability. The making of the holes according to the invention will make inroads into the strength and durability, which is paradoxically an advantage in that a wearer will be discouraged from the medically unsound practice of trying to clean and re-use a disposable contact lens if it is sufficiently fragile.

It is postulated that capillary attraction will for all practical purposes prevent bulk flow of tear fluid through these holes, but they cumulatively account for such an area of the lens surface that oxygen supply from the air by dissolution into tear fluid and diffusion in solution through the static columns of tear fluid in the holes to the eye surface is more than adequate. Blind holes contribute to oxygen transport by lessening the distance through the lens itself which oxygen would have to traverse.

In the case of holes interconnecting the lens surfaces, oxygen permeability is added to the contact lens according to the invention regardless of the other properties of the material comprising the lens.

Such a lens may be characterised as microperforated.

DESCRIPTION OF THE PREFERRED EMBODIMENTS

The invention will now be described by way of example.

The contact lenses used were variously of polymethylmethacrylate and other silicon acrylates, and hydroxyethylmethacrylate (38% water), 9 mm in diameter; and of higher water content materials (hydrogels), the hydrogels being a standard 14 mm in diameter. The hydrogel lenses were perforated in both the xerogel and hydrated states. Holes 50 microns across at the entrance and 100 μm apart were drilled by excimer laser of $\lambda=193$ nm and 20 ns pulse length at 5 Hz. The fluence (flux × time) at the lens (workpiece) was 550 $mJ/cm^2$. The exit diameter of these holes was 25 microns. In other experiments, the holes were 80, 50, 20 and 15 microns at the exit. These holes were drilled in clusters with 34% of the surface area given over to holes. Four clusters of 170 holes each were grouped in a test area with about 23% of the area given over to holes (the difference between 34% and 23% being attributable to the margins between the clusters). In other lenses, the hole centers were 100 μm apart in rows themselves 58 μm apart staggered such that the hole spacing across rows was also 100 μm. In other experiments holes of 25 microns entry diameter have been drilled using projection techniques. The exit diameter of these holes varied from 20 microns in thin sections (less than 150 microns) to 1–2 microns in thick sections (greater than 150 microns). Holes with no taper are ideal since tapering produces two adverse effects. Firstly, tapered holes tend to worsen the optical quality of the lens (increasingly so as the angle of the taper increases) and secondly, the larger, entry hole, limits the hole density.

The contact lenses were 0.05 mm, 0.10 mm, 0.15 mm and 0.20 mm thick. One tapered from 0.05 to 0.50 mm thickness.

The excimer laser used pulsed gas lasers which operate at a number of fixed wavelengths throughout the ultraviolet. Lasing occurs as the result of a pulsed electrical discharge occuring in a high pressure gas. The commonly used three-component gas mixture is made up mostly of a buffer gas such as neon, a smaller amount of a rare gas such as argon, krypton or xenon, and a trace amount of a halogen donor such as hydrogen chloride or fluorine. The combination of rare gas and halogen determine the output wavelength, with the three most powerful excimer lasers being argon fluoride (ArF) at 193 nm, krypton fluoride (KrF) at 248 nm, and xenon chloride (XeCl) at 308 nm. Excimer lasers operate only in a pulsed mode, with pulse durations typically of the order of ten nanoseconds, and output energies per pulse of a few hundred millijoules. This is a unique combination of ultraviolet output and high peak power, and can remove material through the process of ablation. This non-thermal mechanism differs markedly from thermal processes such as melting and vaporization that are commonly associated with other types of laser materials processing. With excimer laser, material can be removed with very high precision and with virtually no heat-affected zone in the surrounding regions of the contact lens.

It is distinguished from other types of industrial laser processing in which a tightly focussed spot is scanned across the workpiece, resulting in only one hole being drilled at a time; excimer lasers are best utilized in a broad beam mode. Therefore the complex patterns of holes in the contact lens is defined by mask imaging rather than by intricate movements of the beam or workpiece.

The mask intercepts the excimer laser beam, which is much broader than a contact lens and continues its path in parallel and now imagewise format; it is only then focussed by a lens or other optical system to a reduced-size image on the contact lens to be microperforated. This reduction allows for great accuracy in the product without imposing impossibly fine tolerances on the mask.

An important factor to be taken into account when drilling curved surfaces is the depth of focus of the laser system. This is another factor which limits the size of the drilled area. Holes of 50 microns have been drilled in a contact lens with the laser system having a 6× de-magnification (i.e. using a 300 micron-hole mask). The depth of focus of this system was 300 microns.

From this result it can be calculated that the theoretical maximum diameter of the drilled zone where all of the holes are in focus is 2.17 mm. This assumes that the focal plane is flat. In fact, it is found that the focal plane is convex as seen by the target. This obviously reduces the effective diameter of the drilling zone on convex lenses.

There are two possible approaches that can be taken to maximise the diameter of the drilling zone:
a) drill the concave side of the lens
b) change the shape of the focal plane using optical components.

Both of these are practical propositions.

The spacing, or pitch, between holes may be constant across the lens or alternatively it may vary in proportion to the lens thickness. This approach would tend to a more uniform distribution of oxygen transmissibility and hence improved corneal health. This is particularly important in high minus power lenses since, by design, the cross-sectional thickness of the lens varies considerably, with the thickest portion being located in the mid-periphery. For practical purposes, such as ensuring adequate mechanical coherence of the lens, its outermost rim, up to ½ mm or 1 mm from the periphery, may be left unperforated.

There may be clinical advantages to drilling holes part-way through the contact lens. For example, if, as had been suggested, the primary cause of discomfort in fenestrated contact lenses is the eyelid rubbing over the edge of the holes, this could be avoided if the lens was drilled part through from the concave side thus leaving the convex side unbroken. This benefit must be balanced against any reduction in oxygen transmissibility which may occur by leaving a thin membrane intact at the bottom of each micro-fenestration. This part-drilled lens, if preloaded with medicament, is ideal for controlled and sustained-release dosage of medicament to or via the cornea of the eye. The eyelid could be correspondingly treated using contact lenses part-way drilled from the convex side. A hydroxyethyl methacrylate lens (38% water) -2 dioptres and 14 mm diameter, central thickness 0.06 mm and concave curve of 8.4 mm radius was mounted on a polypropylene ball. This is a very typical contact lens.

An excimer laser pulsing at 5 Hz with an output of $1J/cm^2$ was focussed through a mask to a 'demagnification' of $\times 6$ onto a sector of the lens. 120 pulses were needed to drill holes through the lens, and samples were made using 50, 70, 80, 90, 100, 120 and 150 pulses. The mask, as projected onto the lens being drilled, had a 24° sector (leaving the central 8 mm diameter and the outermost rim of about ½ mm of the lens undrilled) containing 25 μm diameter circular holes spaced so that holes accounted for half the area of the sector, thus about 6600 holes per sector. The lens was rotationally indexed to drill ten equispaced sectors, although of course fifteen could have been accommodated, and indeed 14 or 15 would be preferred in production lenses.

A similar lens where the holes were 6 μm in diameter could thus be drilled to accommodate just over one million holes without encroaching on the most optically critical central part of the lens. However, as mentioned above, a certain hole density in that central part can be acceptable, such as up to about 0.6 mm² altogether.

We claim:

1. A contact lens comprising a central area of diameter of at least 5 mm and holes of exit diameter of at least one micron and an exit area not exceeding $5 \times 10^{-4}$ mm² going part or all the way from one lens surface to the other, said holes being distributed so that no holes are present in said central area, said holes being in sufficient number to account for at least 5% of the area of the lens.

2. A contact lens according to claim 1, wherein the holes account for at least 10% of said area.

3. A contact lens according to claim 1, wherein the holes account for at least 15% of said area.

4. A contact lens according to claim 1, wherein the holes account for at least 20% of said area.

5. A contact lens according to claim 1, wherein the holes account for at least 25% of said area.

6. A contact lens according to claim 1, wherein the holes account for at least 30% of said area.

7. A contact lens according to claim 1, wherein the holes account for at least 35% of said area.

8. A contact lens according to claim 1, wherein the holes account for at least 40% of said area.

9. A contact lens according to claim 1, wherein the holes are smaller than 150 μm in diameter.

10. A contact lens according to claim 9, wherein the holes are smaller than 100 μm in diameter.

11. A contact lens according to claim 9, wherein the holes are smaller than 50 μm in diameter.

12. A contact lens according to claim 9, wherein the holes are smaller than 30 μm in diameter.

13. A contact lens according to claim 9, wherein the holes are smaller than 10 μm in diameter.

14. A contact lens according to claim 1, wherein the holes are each under $50 \times 10^{-5}$ mm² in area.

15. A contact lens according to claim 14, wherein the holes are each under $10 \times 10^{-5}$ mm² in area.

16. A contact lens according to claim 14, wherein the holes are each under $5 \times 10^{-5}$ mm² in area.

17. A contact lens according to claim 14, wherein the holes are each under $2 \times 10^{-5}$ mm² in area.

18. A contact lens according to claim 9, wherein the holes are in a variety of sizes.

19. A contact lens according to claim 1, wherein there are at least 2000 of said holes.

20. A contact lens according to claim 19 wherein there are over 5000 of said holes.

21. A contact lens according to claim 19, wherein there are over $10^4$ of said holes.

22. A contact lens according to claim 19, wherein there are over $5 \times 10^4$ of said holes.

23. A contact lens according to claim 19, wherein there are over $10^5$ of said holes.

24. A contact lens according to claim 19, wherein there are over $5 \times 10^5$ of said holes.

25. A contact lens according to claim 19, wherein there are over $10^6$ of said holes.

26. A contact lens according to claim 1, wherein over at least part of the lens there are at least 100 holes/mm².

27. A contact lens according to claim 1, wherein all the holes interconnect the two lens surfaces.

28. A contact lens according to claim 1, wherein some of the holes interconnect the two lens surfaces and some go only part way from one lens surface towards the other.

29. A contact lens according to claim 1, wherein all the holes go only part way through the thickness of the lens.

30. A contact lens according to claim 28, wherein all the holes extending part way from one lens surface towards the other start from one lens surface.

31. A contact lens according to claim 30, wherein said one lens surface is the concave surface.

32. A contact lens according to claim 28, wherein some of the holes extending part way from one length surface towards the other start from one lens surface and the others from the other.

33. A contact lens according to claim 1, wherein the holes are provided over the whole area of the lens.

34. A contact lens according to claim 1, wherein a peripheral part of the lens outside said central region has holes going part or all the way from one lens surface to the other in sufficient number to account for at least 5% of the area of the lens.

35. A contact lens according to claim 34, wherein substantially no holes are provided elsewhere than said peripheral part.

36. A contact lens according to claim 33, wherein the holes are provided substantially uniformly over the specified area.

37. A contact lens according to claim 1, wherein the holes are machined by excimer laser.

38. A contact lens according to claim 37, wherein the holes are drilled in one sector of the lens at a time.

39. A contact lens according to claim 37, wherein the excimer laser is applied through a mask and the masked laser beam then focussed on the lens.

40. A contact lens according to claim 1, made of polymethylmethacrylate, hydroxyethyl methacrylate or hydrogel.

41. A contact lens according to claim 1, whose holes contain medicament.

42. A contact lens according to claim 1, wherein said diameter of said central area is 5–11 mm.

* * * * *